US006903822B2

(12) United States Patent
Kakuho et al.

(10) Patent No.: US 6,903,822 B2
(45) Date of Patent: Jun. 7, 2005

(54) APPARATUS FOR AND METHOD OF MEASURING FUEL DENSITY IN AN ENGINE

(75) Inventors: Akihiko Kakuho, Yokosuka (JP); Teruyuki Itoh, Tokyo (JP); Yutaka Hashidume, Yokosuka (JP)

(73) Assignee: Nissan Motor Co., Ltd., Yokohama (JP)

( * ) Notice: Subject to any disclaimer, the term of this patent is extended or adjusted under 35 U.S.C. 154(b) by 400 days.

(21) Appl. No.: 10/175,228

(22) Filed: Jun. 20, 2002

(65) Prior Publication Data

US 2002/0196443 A1 Dec. 26, 2002

(30) Foreign Application Priority Data

Jun. 22, 2001  (JP) ........................................ 2001-189755

(51) Int. Cl.[7] ............................. F01N 3/00; G01N 21/61
(52) U.S. Cl. ........................ 356/434; 356/437; 60/285
(58) Field of Search ................................ 356/434, 437, 356/438; 250/343; 60/285

(56) References Cited

U.S. PATENT DOCUMENTS

| 4,541,272 A | * | 9/1985 | Bause ........................ 356/414 |
| 4,560,873 A | * | 12/1985 | McGowan et al. .......... 250/343 |
| 5,252,060 A | * | 10/1993 | McKinnon et al. ......... 356/437 |

FOREIGN PATENT DOCUMENTS

JP           11-51866         2/1999

* cited by examiner

Primary Examiner—Richard A. Rosenberger
(74) Attorney, Agent, or Firm—Foley & Lardner LLP

(57) ABSTRACT

A measuring light of specific wavelength, which is selectively absorbed by fuel, is transmitted through a measuring passage in a combustion chamber of an engine, to be received by a light receiving element, and intensity of the measuring light of specific wavelength received by the light receiving element is detected. Intensity of the measuring light having transmitted through the measuring passage is calculated, correcting the intensity of the light of specific wavelength detected when transmitting the measuring light through the measuring passage, with the intensity of the light of specific wavelength detected when intercepting the measuring light from transmitting through the measuring passage, while switching between the transmission of the measuring light through the measuring passage and the interception of the measuring light, and transmittance of the measuring light is calculated, based on the intensity of the measuring light before transmitting through the measuring passage and the intensity of the measuring light having transmitted through the measuring passage, so that fuel density in air-fuel mixture in the measuring passage is calculated based on the transmittance. Hereby, the fuel density can be accurately measured by removing an influence by the thermal radiation in the interior of the combustion chamber.

11 Claims, 4 Drawing Sheets

APPARATUS FOR AND METHOD OF MEASURING FUEL DENSITY IN AN ENGINE

BACKGROUND OF THE INVENTION

1. Field of the Invention

The present invention relates to a technology for measuring fuel density in the interior of a combustion chamber of an engine (an internal combustion engine). More specifically, the present invention relates to an apparatus for and method of measuring fuel density in air-fuel mixture supplied to the combustion chambers of an engine.

2. Description of the Related Art

For example, Japanese Laid-open Patent publication No. 11-51866 discloses an apparatus for measuring fuel density in the interior of a combustion chamber, by passing a measuring beam of light of a specific wavelength, which is selectively absorbed by the fuel, through a measuring passage provided in the interior of the combustion chamber, and receiving the measuring beam of light at a light receiving element, to detect the intensity of the received beam of light.

In the described apparatus, the intensity of the measuring beam of light before transmitting through the measuring passage and the intensity of the beam of light after having passed through the measuring passage are introduced in a known logical equation on absorption extinction to perform the calculation of the fuel density.

Nevertheless, even at the timing of measuring the fuel density conducted prior to the start of combustion, there are various kinds of thermal radiations within the combustion chamber of an engine. Thus, the thermal radiations might include radiant light having wavelength identical with that of the measuring light for measuring the fuel density. Therefore, if such radiant light is received by the light receiving element, it is impossible to accurately detect the intensity of the measuring light after having passed through the combustion chamber, which corresponds to the fuel density to be measured. Accordingly, accurate measurement of the fuel density or the air-fuel ratio in the air-fuel mixture cannot be achieved.

In the case where an intensity of light is measured, in order to remove any adverse influence given by background noise, a method is known, in which the light guided to a detector is subjected to chopping at a constant cycle. However, if this method is applied to the measuring of the fuel density, in order to accurately remove the influence by thermal radiation within combustion chambers, which momently varies in response to a change in a crank angle position, the cycle for the chopping must be extremely made short. Thus, it is impossible to adopt this method for measuring fuel density in an engine.

SUMMARY OF THE INVENTION

Therefore, an object of the present invention is to provide a technique for achieving precise measurement of fuel density in air-fuel mixture by removing any adverse influence due to the afore-mentioned thermal radiation.

In order to achieve the above-mentioned object, the present invention takes such a constitution that a measuring light including a specific wavelength, which is selectively absorbed by fuel, transmits through a measuring passage in a combustion chamber of an engine to be received by a light receiving element, intensity of the light including the specific wavelength received by the light receiving element is detected as the first light-intensity by a light-intensity detector and also intensity of the light of specific wavelength is detected as the second light-intensity by the light-intensity detector while the introduction of the measuring light into the measuring passage being intercepted by an interception controller, and intensity of the measuring light having transmitted through the measuring passage is calculated based on the first light-intensity and the second light-intensity, so that fuel density in the interior of the combustion chamber is calculated based on the intensity of the measuring light having transmitted through the measuring passage and intensity of the measuring light before transmitting through the measuring passage.

According to the above-mentioned constitution of the present invention, the fuel density can be precisely measured while removing any adverse influence provided by the thermal radiation in the interior of the combustion chamber of the engine.

The above and other objects, features, aspects, and advantages of the present invention will become apparent to those skilled in the art from the following detailed description, which discloses a preferred embodiment of the present invention with reference to the accompanying drawings.

DETAILED DESCRIPTION OF THE PREFERRED EMBODIMENT

Figure 1:
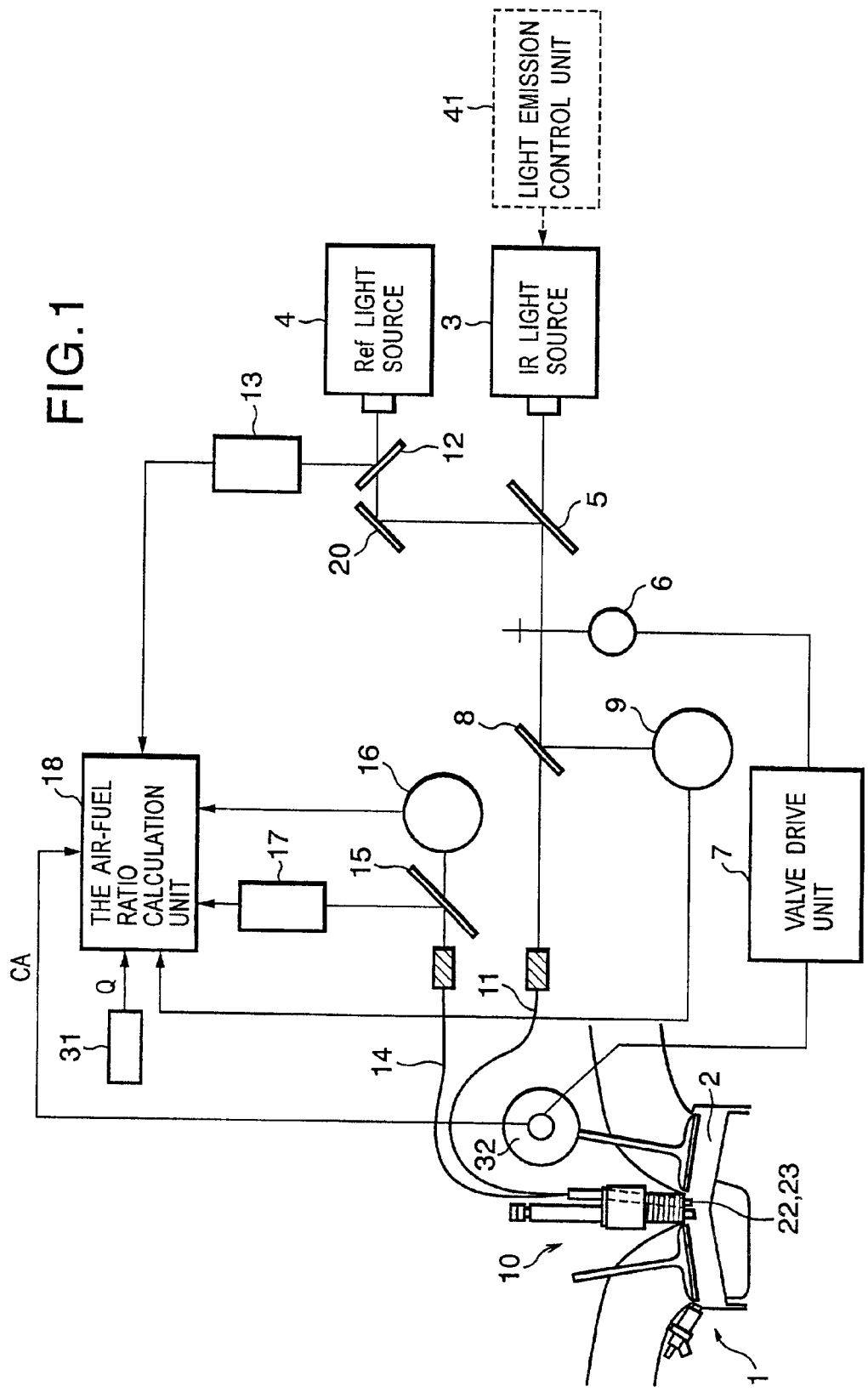
FIG. 1 is a diagrammatic block diagram illustrating en entire construction of a fuel density measuring system according to an embodiment of the present invention.

Referring to FIG. 1, an engine (an internal combustion engine) 1 is provided with combustion chambers 2, one of which is typically shown, and an IR light source (an infrared light source) 3 is provided for irradiating a beam of light having a specific wavelength, which allows the light to be selectively absorbed by fuel injected into the combustion chamber 2.

Namely, the IR light source 3 irradiates, as s measuring light, a beam of infrared light having specific wavelength of 3.39 $\mu$m which is selectively absorbed by the hydrocarbon binding and is not affected by other molecular bindings.

Therefore, the infrared light having the above-mentioned specific wavelength is suitable for measuring an air-fuel ratio of an engine, which employs as its fuel, either a gasoline containing therein a lot of saturated hydrocarbon or a natural gas. The IR light source 3 should be suitably constituted by a He—Ne-laser (helium-neon laser). However, the IR light source 3 may be constituted by heat generating element such as a heater and a laser having another specific wavelength, which is absorbed by another component in the fuel.

Further, an Rf light source 4, which irradiates a light having wavelength of 633 nm, which is not absorbed by the hydrocarbon binding, is arranged in addition to the IR light source 3. Although the light having the wavelength of 633 nm cannot be absorbed by the hydrocarbon bindings, it may be used as a reference light for judging that a reduction in the receiving intensity detected by a fuel-intensity sensor results from dispersion of a part of the measuring light caused by liquid drops but does not result from the fact that the fuel vapor is rich. More simply, the Rf light source might be omitted for curtailment of the manufacturing cost.

At a forward position in a light passage for the light irradiated from the IR light source 3, there is provided a shut-off valve 6 via a dichroic mirror 5. The shut-off valve 6 consists of a solenoid valve, which is capable of operating so as to shut the light passage when it receives a drive pulse from a valve drive unit 7. Namely, the shut-off valve 6 and the valve drive unit 7 constitute an interception controller switchingly controlling the introduction/interception of the measuring light into the measuring-light passage in the interior of the combustion chamber 2. The valve drive unit 7 supplies drive pulses to the shut-off valve 6 during only a predetermined time period of crank angle including therein ignition timing in a non-measuring combustion cycle in which the density of the fuel vapor is not measured. Against this, in the measuring combustion cycle in which the density of the fuel vapor is measured, the valve drive unit 7 odes not emit any drive pulse. The described controlling of emission of drive pulses is conducted on the basis of crank angle signals issued from a rotary encoder 32 secured to the head of a camshaft of the engine 1. In the described embodiment of the present invention, the non-measuring cycle and the measuring cycle are set so as to alternately take place.

In the light passage extending forward with respect to the shut-off valve 6, a beam splitter 8 is arranged so that a part of the beam of the measuring light incident on the beam splitter 8 enters a second IR detector 9. The second IR detector 9 has a light-receipt face defining a front plane in which a band-pass filter is disposed for permitting only a beam of light having the wavelength of around 3.39 μm to transmit therethrough. Namely, intensity of the measuring light before passing through the combustion chamber is detected by the second IR detector 9. Thus, the light having transmitted through the beam splitter 8 is carried by an optical fiber 11 to a sensor-mounted spark plug 10 arranged in the interior of the combustion chamber 2. For simplicity, as the intensity of the measuring light before passing through the combustion chamber, a pre-measured value may be used as a fixed value.

On the other hand, a beam splitter 12 is arranged at a forward position in a light passage extending from the Rf light source 4, so that a part of the reference light incident on the beam splitter 12 after emitting from Rf light source 4 is reflected to be incident on a second Rf detector 13. The second Rf detector 13 has a light-receipt face defining a front plane in which a band-pass filter is disposed for permitting only a beam of reference light having the wavelength of around 633 nm to transmit therethrough. The reference light having the wavelength of 633 nm and transmitting through the beam splitter 12 is reflected by a mirror 20 so as to be led to and enter the afore-mentioned dichroic mirror 5, and is then led to the sensor-mounted plug 10 together with the measuring infrared light having a wavelength of 3.39 μm.

Figure 2:
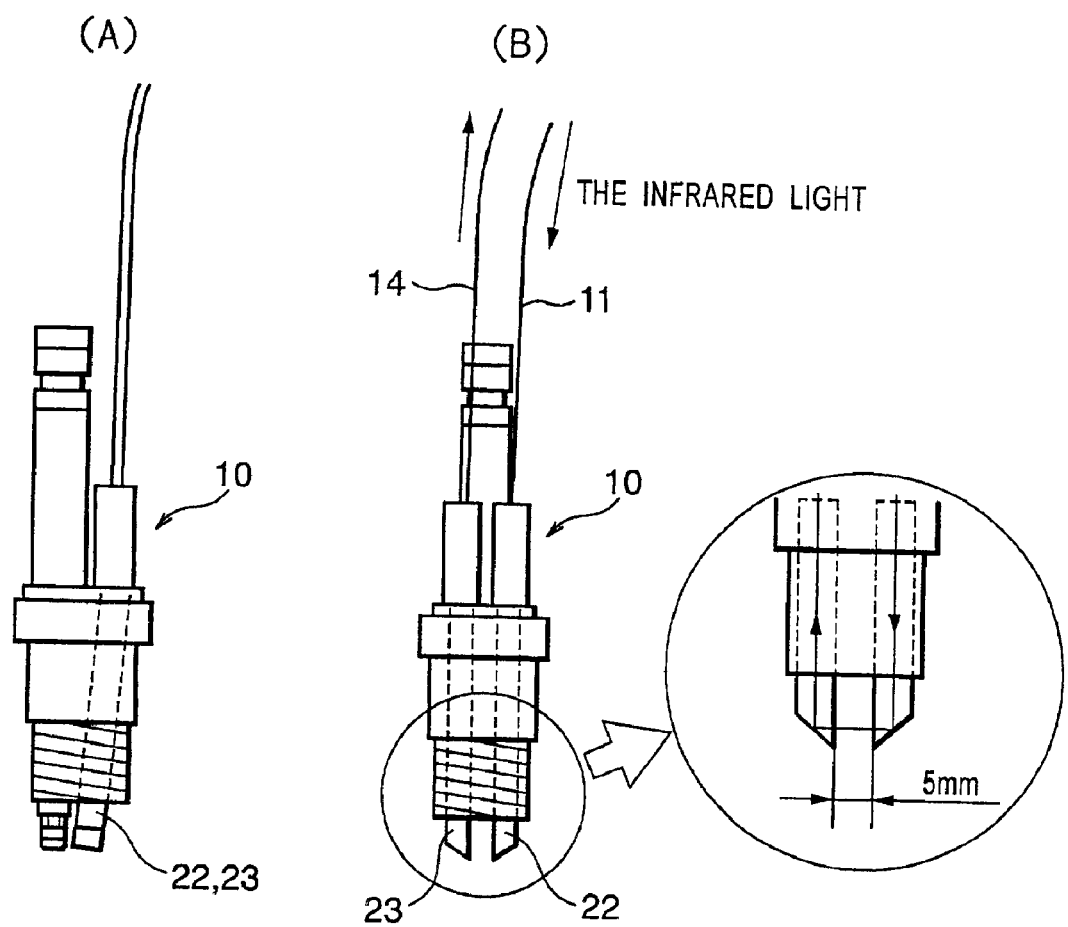
FIG. 2 is a schematic front elevational view, illustrating a portion around a spark plug of the embodiment of the present invention.

FIG. 2 illustrates the construction of the sensor-mounted plug 10 used by the present invention.

The plug 10 is provided with two parallel rods 22 and 23. The two rods 22 and 23 made of sapphire glass that has a good infrared light transmission property. The two sapphire rods 22 and 23 are fixedly attached to the plug 10. The ends of these two rods 22 and 23 are cut at 45° to form an inclined end face, and are subsequently optically polished. Thus, the measuring light is introduced into the rod 22 via the optical fiber 11, and then changes its direction at the inclined end face thereof. Then, the measuring light is introduced into a space in the interior of the combustion chamber 2, and then enters the rod 23. A gap between the two rods 22 and 23 is 5 mm. During transmitting through the space filled with the air-fuel mixture, the measuring light is absorbed and attenuated depending on the density of the fuel vapor being in the space. Thereafter, the measuring light transmits through the rod 23 via the 45° inclined end face thereof, and then enters an outlet side optical fiber 14. Thus, the optical fiber 11 and the sapphire glass rod 22 constitute a measuring light introducing passage, and the light passage between the rods 22 and 23 defines a measuring passage, and the sapphire glass rod 23 constitutes a light receiving element.

Referring again to FIG. 1, the measuring light coming out of the outlet side optical fiber 14 arrives at a beam splitter 15 where it is divided into two beams of measuring light. One of the divided measuring lights enters a first IR detector 16, and the other of the divided measuring light enters a first Rf detector 17. The first IR detector 16 has a light-receipt face in front of which a band-filter of 3.39 μm is arranged, and the first Rf detector has a light-receipt face in front of which a band-filter of 6 33 nm is arranged. Namely, the first IR detector 16 constitutes a light-intensity detector detecting the intensity of light of specific wavelength of 3.39 μm (the wavelength of the measuring light).

A relationship between the light attenuation and fuel density can be defined by the following equation on the basis of the Lamber-Beer rule.

$$\text{Transmittance } T = I/I_0 = \exp(-\epsilon \times C \times L) \quad (1)$$

Where "$I_0$" indicates the intensity of the incident light (intensity of the measuring light before transmitting through the measuring passage), "I" indicates the intensity of the light having transmitted (intensity of the measuring light having transmitted through the measuring passage), "$\epsilon$" indicates an absorption coefficient, "C" indicates the fuel density, and "L" indicates the length of the measuring passage.

It is possible to know the absorption coefficient "$\epsilon$" from fuel description, and the length L is known (5 mm). Therefore, when the transmittance T is calculated from the intensity $I_0$ and I, it is possible to calculate the fuel density C.

An air-fuel ratio calculation unit 18 receives signals output by the respective detectors 9, 13, 16 and 17, and stores the data of the received signals together with parameter n (n={1, 2, 3, . . . }) indicating combustion cycle and parameter CA (CA={CA1, CA2, CA3, . . . , CAm}) indicating crank angle. Further, the air-fuel ratio calculation unit 18 calculates fuel density C on the basis of the equation (1), and converts the calculated fuel density C into a corresponding value of air-fuel ratio. The air-fuel ratio calculation unit 18 constitutes a fuel density calculator.

More specifically, when the unit 18 calculates the air-fuel ratio during the nth combustion cycle (measuring combustion cycle), the unit 18 calculates the intensity $I_0(n)$ of the incident light based on a value Si(n). The value Si(n) is calculated from stored data Si(n, CA) corresponding to signals of the second IR detector 9 by the following equation.

$$Si(n) = \{Si(n, CA1) + Si(n, CA2) + \ldots + Si(n, CAm)\}/m$$

Then, the unit 18 calculates the intensity I(n, CA) of the light having transmitted based on values CSo(n, CA). The values CSo(n, CA) are calculated from stored data So(n, CA) corresponding to signals of the first IR detector 16 and values ASo(n, CA) by the following equation.

$$CSo(n, CA) = So(n, CA) - ASo(n, CA)$$

The values ASo(n, CA) are calculated from stored data So(n−1, CA) and So(n+1, CA) corresponding to signals of the first IR detector 16 by the following equation.

$$AS(n, CA) = \{So(n-1, CA) + So(n+1, CA)\}/2$$

The (n−1)th combustion cycle is an immediately anterior combustion cycle to the nth combustion cycle and the (n+1)th combustion cycle is an immediately posterior combustion cycle to the nth combustion cycle. The (n−1)th combustion cycle and (n+1)th combustion cycle are non-measuring combustion cycle.

Then, the calculated intensity $I_0(n)$ of the incident light and the calculated intensity I(n, CA) of the light having transmitted are substituted in the above-described equation (1) to calculate the fuel density C(n, CA).

Then, the unit 18 calculates an air density within the combustion chamber 2 at every crank angle based on an intake air amount measured by an intake air flow meter 31 and a cylinder volume determined by the crank angle. The air-fuel ratio at every crank angle can be calculated based on the fuel density C(n, CA) and the air density.

Figure 3:
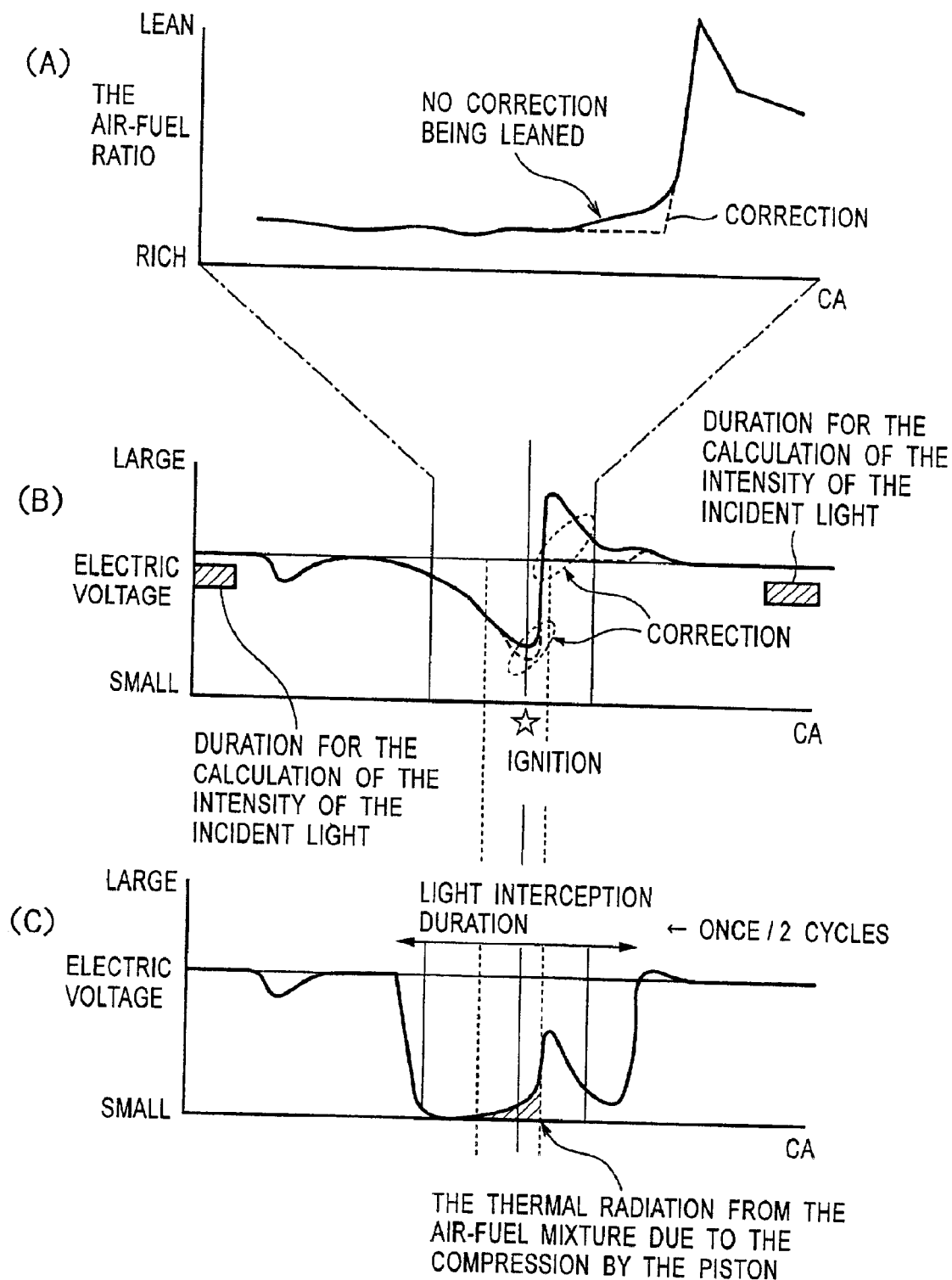
FIG. 3 is a time chart indicating how to correct respective outputs of various detectors provided in the embodiment of the present invention.

(C) of FIG. 3 indicates the signal during the non-measuring combustion cycle, and (B) of FIG. 3 indicates the signal during the measuring combustion cycle, and (A) of FIG. 3 indicates the air-fuel ratio during the measuring combustion cycle.

More specifically, a solid line of FIG. 3-(C) indicates the signal of the first IR detector 16 during the non-measuring combustion cycle. The line is corresponding to the values ASo(n, CA). The shut-off valve 6 intercepts the light passage at crank angle range of compression stroke to exhaust stroke. Due to the compression by a piston, the temperature of the air-fuel mixture within the combustion chamber 2 increases. As a result, thermal radiation within the combustion chamber 2 is increased around ignition timing. This thermal radiation includes infrared light having the specific wavelength of 3.39 $\mu$m. The line of FIG. 3-(C) indicates the intensity of the infrared light included the thermal radiation.

A solid line of FIG. 3-(B) indicates the signal of the first IR detector 16 during the measuring combustion cycle. The line is corresponding to the values So(n, CA). The measuring light is introduced to the measuring passage in the combustion chamber 2. The signal indicates the intensity of measuring light having transmitted through the measuring passage and the infrared light included the thermal radiation. A broken line of FIG. 3-(B) indicates corrected signal. The line is corresponding to the values CSo(n, CA). The line accurately indicates the intensity of measuring light having transmitted through the measuring passage.

A solid line of FIG. 3-(A) indicates the air-fuel ratio obtained by calculating based on the non-corrected signal (the solid line of FIG. 3-(B)). Due to the influence of the thermal radiation, the air-fuel ratio around ignition timing is over-lean in comparison with true air-fuel ratio. A broken line of FIG. 3-(A) indicates the air-fuel ratio obtained by calculating based on the corrected signal (the broken line of FIG. 3-(B)). The line accurately indicates true air-fuel ratio.

At this stage, it should be noted that, by taking into consideration the change in the combustion cycles, the above-described correction is carried out by using an average value among a plurality of light-intercepting cycles, thereby improving accuracy in the measurement of the fuel density by removing adverse influence provided by the change in the combustion cycles.

Figure 4:
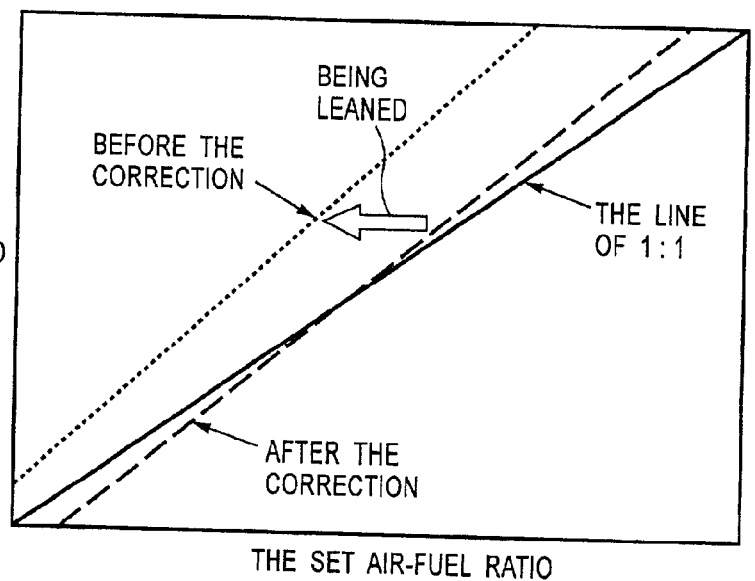
FIG. 4 is a graphical view illustrating the advantageous effect exhibited by the embodiment of the present invention.

The diagram shown in FIG. 4 illustrates the result of the improvement in the measuring accuracy by correcting reduction in the fuel density measuring accuracy caused by the above-described thermal radiation with provision of the non-measuring combustion cycles (the measuring light intercepting cycles). Namely, when the thermal radiation is not taken into consideration, the relationship between the set air-fuel ratio of an engine (the ratio between the intake air amount and the supplied fuel amount at the engine intake port or the exhaust density) and the air-fuel ratio obtained by the infrared absorption method is shifted to a lean side from the line indication the ratio of 1:1. However, when the above-described correction is made, a large improvement in the measuring accuracy can be obtained in the range of any air-fuel ratio.

As described above, according to the present embodiment, since the intensity (second light-intensity) of the light having specific wavelength that is detected by intercepting introduction of a measuring light is used for making correction, it is possible to separate the intensity of the measuring light having transmitted through the light passage (the measuring light after having transmitted through the measuring passage) from the intensity (first light-intensity) of the light having the specific wavelength incident on the light receiving element (the sapphire rod 23), and accordingly the fuel density from which any adverse influence by the thermal radiation is accurately removed, can be calculated.

Further, at the predetermined crank angle CA, since the intensity of the light having the specific wavelength detected during the non-measuring combustion cycle where the measuring light is intercepted is derived from that detected during the measuring combustion cycle where the measuring light is introduced, to thereby calculate the intensity of the measuring light having transmitted, it is possible to accurately remove any adverse influence provided by the thermal radiation, which changes in a change in the crank angle position. Namely, since a major part of the thermal radiation appearing in the interior of the combustion chamber before igniting is based on the thermal radiation generating from the air-fuel mixture of which the temperature is raised by the compression thereof due to the compressive movement of the piston, the intensity of the radiated light at an identical crank angle position, i.e., an identical piston position within the cylinder is approximately unchanged even if the combustion cycle changes.

Further, every time after the implementation of a predetermined number of measuring combustion cycles where introduction of the measuring light is conducted at a crank angle CA at which measurement of the fuel density is requested to conduct, if the non-measuring combustion cycle where the introduction of the measuring light is intercepted is conducted at the same crank angle CA, it is possible to accurately remove any influence by the thermal radiation, which changes in response to a time lapse. Namely, in the interior of the combustion chamber, there exists a bit amount of thermal radiation from the wall surface of the combustion chamber, and the temperature of the wall surface goes up and down in response to the time lapse. Also, when the temperature of the wall surface changes, the temperature of the air-fuel mixture at every identical crank angle also changes. Thus, the measuring combustion cycle and the non-measuring combustion cycle should preferably occur at times close to one another, and therefore the non-measuring combustion cycle should desirably be carried out every time after the implementation of the predetermined number of measuring combustion cycles.

Further, in the present embodiment, the intensity of the measuring light having transmitted is calculated from the intensity of the light having the specific wavelength during the measuring combustion cycle and the average value of a plurality of intensities of the light having the specific wavelength which are detected during the plurality of non-measuring combustion cycles. Thus, it is possible to suppress any adverse influence due to a change in the cycle. Namely, even under a condition such that the temperature of the wall surface of the combustion chamber is unchanged, and the measurement is always carried out at an identical crank angle, there may occur that the thermal radiation within the combustion chamber changes at every cycle due to the other factors, for example, the amount of residual burned gas in the interior of the combustion chamber. Therefore, in order to reduce the influence of the change in cycles, the average value of the plurality of intensities of the light having the specific wavelength, which are detected during the plurality of non-measuring combustion cycles should be used.

Further, according to the present embodiment, since the measuring combustion cycles and the non-measuring combustion cycles are alternately implemented, it is possible to increase the measuring accuracy of the fuel density by implementing the non-measuring combustion cycles at the highest frequencies to correct the measuring value of the fuel density.

Also, in the present embodiment, since the intensity of the measuring light having transmitted (the intensity of the measuring light after having transmitted through the measuring passage) is calculated from the intensity (first light-intensity) of the light having the specific wavelength, which is detected during the measuring combustion cycle and the intensity (second light-intensity) of the light having the specific wavelength, which is detected during the immediately anterior non-measuring combustion cycle, the influence given by the time-lapse change in the thermal radiation can be reduced to the minimum. Particularly, since the intensity of the measuring light having transmitted is calculated from the intensity of the light having the specific wavelength, which is detected during the measuring combustion cycle and the average value of the intensities of the light having the specific wavelength, which are detected during the immediately anterior and posterior non-measuring combustion cycles, it is possible to not only reduce the influence given by the time-lapse change in the thermal radiation to the minimum but also decrease the influence given by the cycle change.

Furthermore, since the introduction of the measuring light and the interception of such introduction of the measuring light are changed over from one another by the opening and closing of the measuring light introducing light passage at a predetermined crank angle, which are performed by the shut-off valve 6 arranged at a position in the measuring-light introducing light passage, the introduction and interception of the light can be achieved by a simple method irrespective of the sort of the light source.

Alternately, as the interception controller, an emission controller 41 may be used to perform ON/OFF control of the emission from the light source (IR light source 3) or the stop of the emission.

It should be understood that the entire contents of the basic Japanese Patent Application No. 2001-189755 filed on Jun. 21, 2001, a convention priority of which us claimed, are herein incorporated by reference.

While only selected preferred embodiments have been chosen to describe and illustrate the present invention, it will be apparent to a person skilled in the art from this disclosure that various changes and modifications will occur herein without departing from the scope of the invention as claimed in the accompanying claims, Further, the foregoing description of the embodiments according to the present invention are provided for illustration only, and not for the purpose of limiting the invention as defined by the accompanying claims and their equivalents.

What is claimed is:

1. An apparatus for measuring density of fuel in an engine comprising:
   a measuring light introducing passage introducing a measuring light to a measuring passage in a combustion chamber of the engine, the measuring light including a specific wavelength which is selectively absorbed by the fuel;
   a light receiving element receiving the measuring light having transmitted through the measuring passage;
   a light-intensity detector detecting intensity of light having the specific wavelength, the light received by the light receiving element being introduced to the light-intensity detector;
   an interception controller intercepting the measuring light from introducing to the measuring passage; and
   a fuel density calculator programmed to:
      calculate intensity of the measuring light having transmitted through the measuring passage by subtracting, from a first light-intensity detected at a predetermined crank angle by the light-intensity detector when the measuring light is introduced to the measuring passage, a second light-intensity detected by the light-intensity detector at the same predetermined crank angle when the measuring light is intercepted by the interception controller; and
      calculate fuel density based on the intensity of the measuring light having transmitted through the measuring passage and intensity of the measuring light before transmitting through the measuring passage.

2. The apparatus according to claim 1, wherein every time after a predetermined number of executions of measuring combustion cycle during which the measuring light transmits through the measuring passage, at a crank angle at which the fuel density is requested to be measured, the interception controller executes non-measuring combustion cycle during which the transmission of the measuring light is intercepted, at the identical crank angle.

3. The apparatus according to claim 2, wherein the fuel density calculator corrects the first light-intensity detected during the measuring combustion cycle with an average value of the second light-intensity detected during a plurality of numbers of non-measuring combustion cycles, to calculate the intensity of the measuring light having transmitted through the measuring passage.

4. The apparatus according to claim 2, wherein the interception controller alternately executes the measuring combustion cycles and the non-measuring combustion cycles.

5. The apparatus according to claim 4, wherein the interception controller calculates the intensity of the measuring light having transmitted through the measuring passage, from the first light-intensity detected during the measuring combustion cycle and the second light-intensity detected during immediately anterior measuring combustion cycle.

6. The apparatus according to claim 4, wherein the interception controller calculates the intensity of the measuring light having transmitted through the measuring passage, from the first light-intensity detected during the measuring combustion cycle and an average value of the second light-intensities detected during immediately anterior and posterior measuring combustion cycles.

7. The apparatus according to claim 1, wherein the interception controller shuts off the measuring light introduction passage, to intercept the measuring light from transmitting through the measuring passage.

8. The apparatus according to claim 1, wherein the interception controller stops the emission of the light source, to intercept the measuring light from transmitting through the measuring passage.

9. The apparatus according to claim 1, comprising a further light-intensity detector detecting intensity of the measuring light before transmitting through the measuring passage.

10. An apparatus for measuring density of fuel in an engine comprising:

a measuring light introducing means for introducing a measuring light to a measuring passage in a combustion chamber of the engine, the measuring light including a specific wavelength which is selectively absorbed by the fuel;

a light receiving means for receiving the measuring light having transmitted through the measuring passage;

a light-intensity detecting means for detecting intensity of light having the specific wavelength, the light received by the light receiving means being introduced to the light-intensity detecting means;

an interception controlling means for intercepting the measuring light from introducing to the measuring passage;

a transmitted measuring light intensity calculating means for calculating intensity of the measuring light having transmitted through the measuring passage, by subtracting, from a first light-intensity detected at a predetermined crank angle by the light-intensity detecting means when the measuring light is introduced to the measuring passage, a second light-intensity at the same predetermined crank angle detected by the light-intensity detecting means when the measuring light is intercepted by the interception controlling means; and a fuel density calculating means for calculating fuel density based on the intensity of the measuring light having transmitted through the measuring passage and intensity of the measuring light before transmitting through the measuring passage.

11. A method of measuring density of fuel in an engine comprising:

transmitting a measuring light including a specific wavelength, which is selectively absorbed by the fuel, through a measuring passage in a combustion chamber of the engine to be received by a light receiving element;

detecting, as a first light-intensity, intensity of light of specific wavelength received by the light receiving element;

detecting, as a second light-intensity, intensity of the light of specific wavelength received by the light receiving element while intercepting the measuring light of specific wavelength from transmitting through the measuring passage;

calculating the intensity of the measuring light having transmitted through the measuring passage by subtracting, from the first light-intensity detected at a predetermined crank angle, the second light-intensity detected at the same predetermined crank angle; and calculating fuel density based on the intensity of the measuring light having transmitted through the measuring passage and intensity of the measuring light before transmitting through the measuring passage.

* * * * *